US008211058B2

(12) United States Patent
Jorna

(10) Patent No.: US 8,211,058 B2
(45) Date of Patent: Jul. 3, 2012

(54) DEVICE FOR INJECTING VETERINARY PRODUCTS TO POULTRY INCLUDING A RETENTION MEMBER HAVING AN ANATOMIC FORM WITH MEANS FOR BRACING A DETECTABLE BONE

(75) Inventor: Anno Jorna, Avrille (FR)

(73) Assignee: Desvac, Pellouailles les Vignes (FR)

( * ) Notice: Subject to any disclaimer, the term of this patent is extended or adjusted under 35 U.S.C. 154(b) by 63 days.

(21) Appl. No.: 12/676,697

(22) PCT Filed: Sep. 5, 2008

(86) PCT No.: PCT/EP2008/061783
§ 371 (c)(1), (2), (4) Date: Jul. 1, 2010

(87) PCT Pub. No.: WO2009/030755
PCT Pub. Date: Mar. 12, 2009

(65) Prior Publication Data

US 2011/0054401 A1 Mar. 3, 2011

(30) Foreign Application Priority Data

Sep. 5, 2007 (FR) ..................................... 07 06206

(51) Int. Cl.
*A61M 37/00* (2006.01)

(52) U.S. Cl. ........ 604/131; 604/130; 604/144; 604/156; 119/713; 119/719

(58) Field of Classification Search .......... 604/130–134, 604/136–139, 143–146, 147; 119/713–714, 119/718–719
See application file for complete search history.

(56) References Cited

U.S. PATENT DOCUMENTS

| | | | | |
|---|---|---|---|---|
| 4,019,513 | A | 4/1977 | Kaniecki | |
| 4,681,565 | A | 7/1987 | Gourlandt | |
| 5,311,841 | A * | 5/1994 | Thaxton | 604/506 |
| 2007/0093747 | A1 * | 4/2007 | Smith | 604/67 |
| 2008/0220022 | A1 * | 9/2008 | Le Gros et al. | 424/258.1 |

FOREIGN PATENT DOCUMENTS

FR 2276839 1/1976

OTHER PUBLICATIONS

International Search Report, mailed Jan. 9, 2003, 2 pages.

* cited by examiner

*Primary Examiner* — Quynh-Nhu H Vu
(74) *Attorney, Agent, or Firm* — Pauly, Devries Smith & Deffner, L.L.C.

(57) ABSTRACT

The invention relates to a device for injecting veterinary products to at least one bird by intramuscular injection, wherein said injection(s) can be carried out in the area of at least one muscle in the vicinity of a bone having a detectable shape in the body of said poultry, said device comprising: a retention member with means for bracing said detectable bone, at least one hole being formed in said retention member; at least one injection needle, said needle(s) being movable across said opening(s); characterized in that the retention member has: an anatomic shape that conforms to a portion of the body of said poultry and inside which is provided said means or bracing the detectable bone, said anatomic shape including a bearing surface for said body at said muscle; at least two contact sensors to be actuated by said poultry and provided on the anatomic shape with at least one on the bearing surface, said opening(s) being provided between said sensors.

16 Claims, 4 Drawing Sheets

DEVICE FOR INJECTING VETERINARY PRODUCTS TO POULTRY INCLUDING A RETENTION MEMBER HAVING AN ANATOMIC FORM WITH MEANS FOR BRACING A DETECTABLE BONE

CROSS-REFERENCE TO RELATED APPLICATIONS

This application is a national stage application under 35 U.S.C. 371 of International Patent Application Serial No. PCT/EP2008/061783, filed Sep. 5, 2008, which claims priority from French Patent Application No. 07/06206, filed Sep. 5, 2007, the disclosure of which is hereby incorporated by reference.

FIELD OF THE INVENTION

The field of the invention is that of veterinary practice assistance devices. More specifically, the invention relates to devices for injecting veterinary products to birds and more specifically to poultry by intramuscular or subcutaneous injection, using at least one movable needle across a hole formed in a retention member of the birds in a muscle close to a detectable bone.

The invention also relates to processes or methods for injecting and/or vaccinating poultry using these devices. The invention further relates to the use of these devices for the vaccination or more generally for the treatment and/or prevention of avian diseases. Finally, the present invention relates to methods and kits for the treatment and/or prevention of avian diseases in birds and more specifically poultry.

BACKGROUND OF THE INVENTION

In the field of poultry farming, it is conventional to need to inject veterinary products, particularly vaccines, to the poultry.

The injections may be performed manually, However, in this case, a vaccination campaign proves to be excessively long. Furthermore, some injections need to be performed with satisfactory precision, as manual execution does not guarantee sufficient and/or consistent precision, particularly as an injection campaign frequently relates to a very large number of birds, implying considerable repetition of the actions of the operator (who needs to take hold of the fowl and perform the injection while holding the fowl firmly) and, consequently, tiredness of the operator liable to result in a lack of precision in the actions carried out.

Therefore, the prior art has proposed devices for assisting with the injection of veterinary products.

In particular, the patent document published under the number FR 2 276 838 is known, relating to a device for the automatic injection of a vaccine in the limb of a fowl comprising:

- an injection syringe;
- means for the retention of the animal to be treated, comprising abutment and gauge members formed by a removable fixed plate having a rectilinear edge and an oblique edge whereon the limb or neck of the bird or other part of the body is placed in a given transverse position and at a given angle in relation to the syringe;
- means for advancing and retracting the syringe for each injection;
- a control member such as a push button protruding slightly on the rectilinear edge of the plate such that the positioning of the animal activates the injection simultaneously.

This technique involves a number of drawbacks including the following:

- the retention means are devised to hold only one limb of the fowl, which limits the applications of the device (since many veterinary products need to be injected into other parts of the body of a fowl);
- the means for holding the limb on the retention means are relatively basic and do not guarantee the presentation of limb of the fowl with a high level of precision;
- the presence of a fowl and the injection is controlled by a type of push button; however, there is no guarantee that the fowl is positioned correctly at the time of injection;
- the push button to be actuated by the positioning of the fowl may also be actuated inadvertently by the operator who may receive an injection, which obviously is to be avoided.

Furthermore, the patent document published under the number FR 2 276 839 is known, relating to a device for vaccinating very small animals such as chicks, comprising

- a syringe attached to the frame of the device and provided with a compressed air cylinder injection system;
- two identical plates forming a groove having an angle of approximately 90° C. for receiving the necks of the chicks. The plates also comprise transverse hollows where the operators position their fingers and on either side of the neck of the chicks so as to hold same during the injection; and
- a compressed air sensor, positioned behind one of the plates, which is blanked when an animal is positioned on the plates and thus controls the cylinder actuation mechanism.

However, this device involves a number of drawbacks including the following:

- it appears to be essentially suitable for the subcutaneous injection in the neck of small farmyard birds such as chicks and;
- it only allows an approximate positioning of the birds on the device and does not offer any precision in relation to the contact area to be injected;
- it likewise does not guarantee operator safety.

According to a further technique described by the patent document published under the number U.S. Pat. No. 4,758,227, a vaccination device comprising a cradle retention member suitable for receiving the body of a fowl, in the vicinity whereof translatably movable injection means are mounted.

The device further comprises a member whereon the breast-bone of the bird is to be supported. This device is particularly suitable for injecting a vaccine into the breast-bone muscles of the bird, on each side. When the fowl is in position, the injection is activated by the operator, using a button or a control pedal.

This technique likewise involves the drawback of not enabling the precise positioning of the fowl in relation to the needles, with the injection thus possibly being carried out in an area of the body of the fowl which is ineffective or even inoperative or hazardous for the animal. Furthermore, the injection may be administered even if the position of the animal is not satisfactory.

Indeed, the injection of a veterinary product, particularly an intramuscular vaccine in the body of the bird must be performed precisely so as to avoid injecting organs or bones close to the target muscles. For example, in the case of the muscles adjacent to the breast-bone of a fowl, the injection must comply with all the following points:

- the injection must not be too low on the body of the poultry, with a view to obligatorily avoiding an injection in the liver of the fowl (which would cause the death of the fowl almost instantaneously);

the depth of the injection must be perfectly controlled to prevent same being performed in the breast-bone (in which case, the injection would be ineffective or practically ineffective);

the injection must not be performed too high on the body of the fowl to avoid administering an injection of the clavicle of the poultry;

the injection must be administered with a predefined constant depth (in the region of 10 mm for hens of ten weeks and more).

Furthermore, the injections must be performed such that the return of the syringes does not occur before the product has been injected entirely. In particular, in the case of the injection of two separate products, the difference in viscosity between the two products may require specific injection kinematics to enable the satisfactory diffusion of the products in the muscle.

In any case, the technique described by the document U.S. Pat. No. 4,758,227 cannot guarantee high-quality mass vaccination of poultry in terms of all the points cited above.

It is noted that the problem of poultry positioning precision is accentuated all the more as, generally, the operator performing the vaccination performs these actions at a high speed, on adult poultry that are difficult to handle, or if the areas to be injected are not readily visible for the operator.

A further technique described by the patent document published under the number U.S. Pat. No. 5,312,353 is known, relating to a device for vaccinating chicks. According to this technique, the device comprises a gauge comprising two surfaces at right angles, defining a space wherein the head and neck of a chick are to be introduced, each of the two surfaces having a sensor for detecting the presence of a chick, the simultaneous activation of both sensors activating vaccination.

Once again, this technique does not enable precise positioning of the poultry in the device and thus does not guarantee high-quality and/or consistent quality injection.

Furthermore, the positioning gauge has a very basic shape, inside which any part of a fowl could be introduced, while enabling the simultaneous actuation of both sensors, and thus the activation of vaccination.

According to a further technique described by the patent document published under the number FR 2 839 245, a poultry sanitary treatment station is proposed having a cradle comprising an area for receiving and supporting the breast of the fowl wherein an opening is formed to insert a syringe needle and incorporating a presence detector enabling, or not, the operation, by a separate control, of means for moving and actuating the syringe. Furthermore, the device comprises means for cutting the beak of the fowl.

The positioning of the fowl in the cradle is performed when the breast is present in the reception area and the beak of the fowl presented facing the corresponding cutting means.

It is noted that such as device only allows approximate positioning of the fowl in relation to the injection means.

In any case, this device does not guarantee injection quality as defined by the points listed above.

SUMMARY OF THE INVENTION

The aim of the invention is particularly that of remedying the drawbacks of the prior art.

More specifically, the aim of the invention is that of providing a device for administering injections of veterinary products in the body of a bird and more specifically of a fowl guaranteeing optimal quality of the injection carried out.

A further aim of the invention is that of providing such a device guaranteeing such quality including high injection speeds.

A further aim of the invention is that of providing such a device which can be used by non-specialised operators while maintaining the quality of the injections carried out.

A further aim of the invention is that of providing such a device which guarantees operator safety.

A further aim of the invention is that of providing such a device which has a simple design and is easy to use.

These aims, along with others which will emerge hereinafter, are achieved by means of the invention which relates to a device for injecting veterinary products to at least one fowl by intramuscular injection using at least one injection needle, wherein said injection(s) can be carried out in the area of at least one muscle in the vicinity of a bone having a detectable shape in the body of said fowl, said device comprising a retention member with means for bracing said detectable bone, at least one hole formed in said retention member, said needle(s) being movable across said hole, said retention member having an anatomic shape that conforms to said body of said fowl and inside which said bracing means are provided, said anatomic shape comprising a bearing surface for said body at said muscle, at least two contact sensors to be actuated by said fowl and provided on said anatomic shape with at least one on said bearing surface, said hole(s) being provided between said sensors.

The device according to the invention may be used for the injection, vaccination and/or treatment of all types of birds such as conventionally poultry, hens, ducks, turkeys, guinea fowl, quail, geese, pigeons or parrots.

The device according to the invention may in particular be advantageously used in hen farms (for breeding or laying). Indeed, the number of hens in these farms is considerable and it is frequently necessary to conduct vaccination campaigns rapidly, with high reliability in view of the significant risks of contagion in the farm.

In this way, a device according to the invention can be used to administer injections to poultry (or more generally to birds) in accordance with the quality criteria mentioned above, consistently between fowl, including at high speeds.

Indeed, the anatomic shape of the retention member enables reliable and precise positioning of the bird opposite the needle(s).

Since the retention member is designed to conform to the shape of the body of the fowl, the operator, even if not specialised, can readily and rapidly see and/or know how to present the fowl in the device.

This is particularly useful for adult poultry (or any other bird) such as adult hens, for which the anatomic reference area to be positioned by the operator on the retention area is not readily visible.

The detection means consist of at least two sensors located on the anatomic shape, with at least one on the bearing surface of the muscle to be injected situated in the vicinity of the detectable bone, making it possible to detect whether the reference anatomic area (i.e. the part of the body to be injected) is positioned correctly on the complementary anatomic shape thereof. The sensors or detection means positioned in this way can only be activated if the reference anatomic area of the bird is positioned correctly. The operator is thus guaranteed not to receive untimely injections in the event of improper operation of the device according to the invention.

Consequently, the anatomic shape makes it possible, firstly, to obtain a satisfactory general positioning of the fowl: since the anatomic shape conforms to a part of the body of the fowl, it is quickly and obviously clear to the operator which part of the fowl needs to be introduced into the retention member, with it being impossible or practically impossible to present the fowl in another way. The anatomic shape can thus conform to any suitable part of the body of the fowl, such as for example the breast or the thorax, the dorsal side at the wings or the pelvis at the legs.

Furthermore, the general positioning is followed by detailed positioning, using the means for bracing the detectable bone, said bracing means forming a type of abutment against which the detectable bone of the fowl is to be pressed. At this stage, the body of the fowl is thus correctly presented in the device, with the target areas to be injected using the needle(s) presented correctly opposite the hole(s) formed in the retention member enabling the insertion of the needle(s). The detectable bones may for example be the breast-bone wherein the pectoral muscles and alar muscles are attached, or the cranial entry of the thorax, the pectoral girdle and the clavicle wherein the alar muscles are attached, or the coxal muscles of birds where the leg muscles are inserted with a reference point at the abdomen formed by the ilioischial foramen.

Among the quality criteria for an injection, the injection depth is a decisive point.

This quality criterion is guaranteed by means of the invention, due to the presence of at least two sensors on either side of the hole(s). Indeed, the travel of the needles can readily be determined according to the bearing surface against which the body of the fowl is to be applied. When the part of the body of the fowl in which the target area to be injected is situated is pressed correctly against the corresponding bearing surface, it is clear that the injection depth is that expected. The presence of sensors on either side of the passage for the needle ensures the detection of pressing against the corresponding surface, whereas the part of the body between the sensors is also pressed against the bearing surface.

It is thus understood that the device according to the invention helps, in an optimised manner, meet poultry injection quality criteria, with simple, quick and unambiguous procedures by the operator.

Furthermore, the injection is not activated in the event of incorrect positioning of the fowl in the device. Moreover, as will emerge more clearly hereinafter, the device according to the invention limits the risks of the operator inadvertently injecting him/herself with the product considerably.

Obviously, the principle of the invention may be used for any type of birds such as, in particular, poultry (for example, hens, ducks, turkeys, guinea fowl, quail, geese, pigeon, parrots, or any other farmyard birds) and/or other parts of the body, for example selecting as the detectable bone (for example, the breast-bone, a detectable bone of a limb joint, such as the thigh or wing, the pectoral girdle and the clavicle, the coxal bones, or the ilioischial foramen).

According to one preferential application, said anatomic shape corresponds at least partially to the breast of said fowl, said bracing means forming a space for receiving and abutting a fowl breast.

According to one advantageous solution of this preferential application, said anatomic shape extends from said space for receiving and abutting a fowl breast to a complementary bracing protuberance against which a cavity between the clavicles of said fowl is to be pressed.

Such a protuberance helps position the fowl precisely in the retention member and also provides a complementary reference point for the operator.

Advantageously, said anatomic shape extends from said space for receiving and abutting a fowl breast to a complementary bearing surface corresponding to the shape of at least one thigh of said fowl.

In this way, the retention member extends relatively broadly, from the space between the clavicles of the fowl to the thighs thereof, facilitating, for the operator, the work to hold the fowl in the device.

According to one particular embodiment, the device has two holes each forming a passage across which an injection needle is movable, said bracing means extending between said holes.

In this way, the device enables a dual injection of veterinary products which is becoming a routine practice.

Furthermore, when the detectable bone consists of the breast-bone, each of the holes is positioned in the vicinity of the main reference means consisting of the bracing means, and particularly enables targeted injections specifically on either side of the breast of the fowl.

According to one advantageous feature of the invention, one of said sensors is positioned in said bracing means.

According to the application of the device where the bracing means are to receive the breast-bone, said means consist of a cavity of a specific shape formed in the anatomic shape. The presence of a sensor in said cavity makes it possible not only to detect the presence of the breast-bone, but also limits the risk of the operator being injected with the product. Indeed, it is very unlikely for an operator to introduce for example part of his/her hand inside the bracing means, while actuating the other sensor present on the bearing surface.

If the device is planned for dual injection, it preferentially comprises three contact sensors to be actuated by said fowl, said three sensors being arranged in a V shape, the base of said V shape being occupied by said sensor positioned in said bracing means.

The precise positioning of the fowl is thus provided in relation to each hole, a pair of sensors being associated with each hole, one sensor (that positioned in the bracing means) being common to both pairs of sensors.

According to a further advantageous feature of the invention, said retention member is removably mounted on a sensor incorporating means for driving said needle(s).

In this way, it is possible to change the retention member easily and quickly according to the type of bird (for example, a fowl such as a breeding hen has a larger build than a laying hen) and/or the part of the body to be held on the device.

According to a further feature, said casing has a rear hatch for accessing said drive means.

In this way, within the scope of any maintenance operations, access inside the casing is obtained from the rear, which limits the risks of injury for the technician against the injection needle(s) pointing towards the front of the device.

According to a further feature, said hole(s) have an oblong shape, said device comprising the means for adjusting the position of said needle(s) in relation to said hole(s).

In this way, it is possible to adjust the position of the needles according to the target areas on the body of the birds, without having to modify or replace the retention member.

The present invention also relates to processes or methods for injecting and/or vaccinating poultry comprising steps consisting of taking hold of said poultry by taking same by the wings and legs and positioning same on the device according to the invention such that the part of the body of the fowl completely conforms to the anatomic shape of the retention member, and pressing said fowl positioned in this way against said retention member such that a reference bone close to the muscle to be injected is pressing against the end of the bracing means and can thus actuate the sensors, the movement of the syringes and the injection of the veterinary product(s). It is thus possible to inject with a high level of precision various parts of the body of the fowl using a reference bone for the correct positioning of the poultry on the device as described above.

This injection process is particularly advantageous for vaccinating and/or treating poultry for example against avian influenza, SARS, avian malaria, Newcastle disease, mycoplasmosis, cholera, Gumboro disease, chicken pox, candidiasis, aspergillosis, salmonellosis, enteritis, bronchitis, pancreatitis, Marek disease, diseases caused by reovirus and/or astrovirus infections, leucosis, or infectious anaemia. The process or method according to the present invention may furthermore be used for preventive purposes to prevent infections and contaminations particularly in bird farms.

The present invention further relates to the use of the devices as described above for injecting and/or treating infected poultry with suitable veterinary compositions in relation to the avian diseases and this treating and/or preventing said diseases. In addition, the poultry vaccination device according to the present invention is useful for ensuring the prevention of avian diseases. Finally, the present invention relates to the methods and kits for treating and/or preventing avian diseases in poultry.

As described above, all types of birds and particularly poultry such as hens, ducks, guinea fowl, quail, geese, pigeons, or parrots may be vaccinated and/or treated in this way.

As mentioned above, the term veterinary product refers to any compound to be administered to poultry as a preventive and/or therapeutic and/or necessary treatment for the welfare of the poultry and for example, without being exhaustive, a vaccine, vitamins, nutritional supplements, antibiotics.

The invention further relates to an avian injection or vaccination kit comprising the device as described above, and a series of removable retention members having varied anatomic shapes suitable for the different parts of the body and detectable bones of poultry. The kit may advantageously further comprise a set of syringes, vials, bags or suitable packaging for veterinary products and/or vaccines. The avian injection or vaccination kit may also comprise a technical data sheet and instructions on the vaccination and/or treatment methods and on the use of said device.

BRIEF DESCRIPTION OF THE DRAWINGS

Other features and advantages of the invention will emerge more clearly on reading the following description of a preferential embodiment of the invention, given as an illustrative and non-limitative example, and the appended figures wherein.

DETAILED DESCRIPTION

As specified above, the principle of the invention lies in the association with a device for injecting avian veterinary products of a retention member wherein the anatomic shape conforms to the body of the fowl and including means for bracing a detectable bone, particularly the breast-bone of the fowl, the device comprising sensors for verifying that the fowl is pressing correctly against a bearing surface of the anatomic shape in the vicinity of one or a plurality of holes across which an injection needle is translatably movable.

It is noted that a device according to the principle of the invention may be applied to different poultry (and more generally to birds) and/or to different injection target areas.

The device described hereinafter is suitable for injecting veterinary products, particularly vaccines, in the wing muscles extending along the breast-bone of a fowl.

Figure 1:
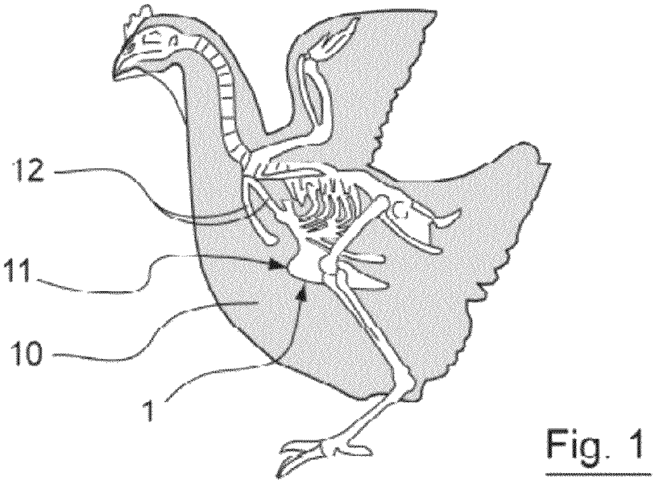
FIG. 1 is a schematic representation of a skeleton of a hen.

With reference to FIG. 1, it is noted that the skeleton of a hen comprises a breast-bone 1 along and either side of which extend the wing muscles, said breast-bone 1 having one end 11 which is detectable by touch across the breast 10 of the hen. The skeleton of a hen also comprises clavicles 12 between which a space also detectable by touch extends.

Hereinafter in the description, the breast-bone 10, and particularly the end 11 thereof, forms a detectable bone according to the invention.

Figure 2:
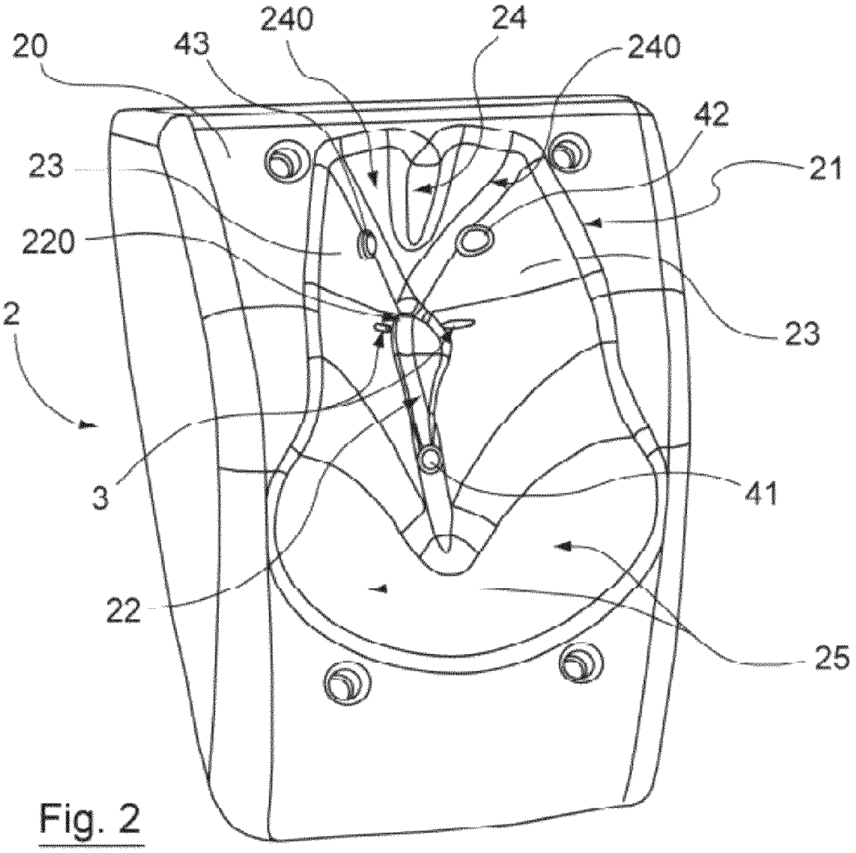
FIGS. 2 and 3 are perspective views of a retention member of a device according to the invention, for a breeding hen and for a laying hen respectively.
Figure 3:
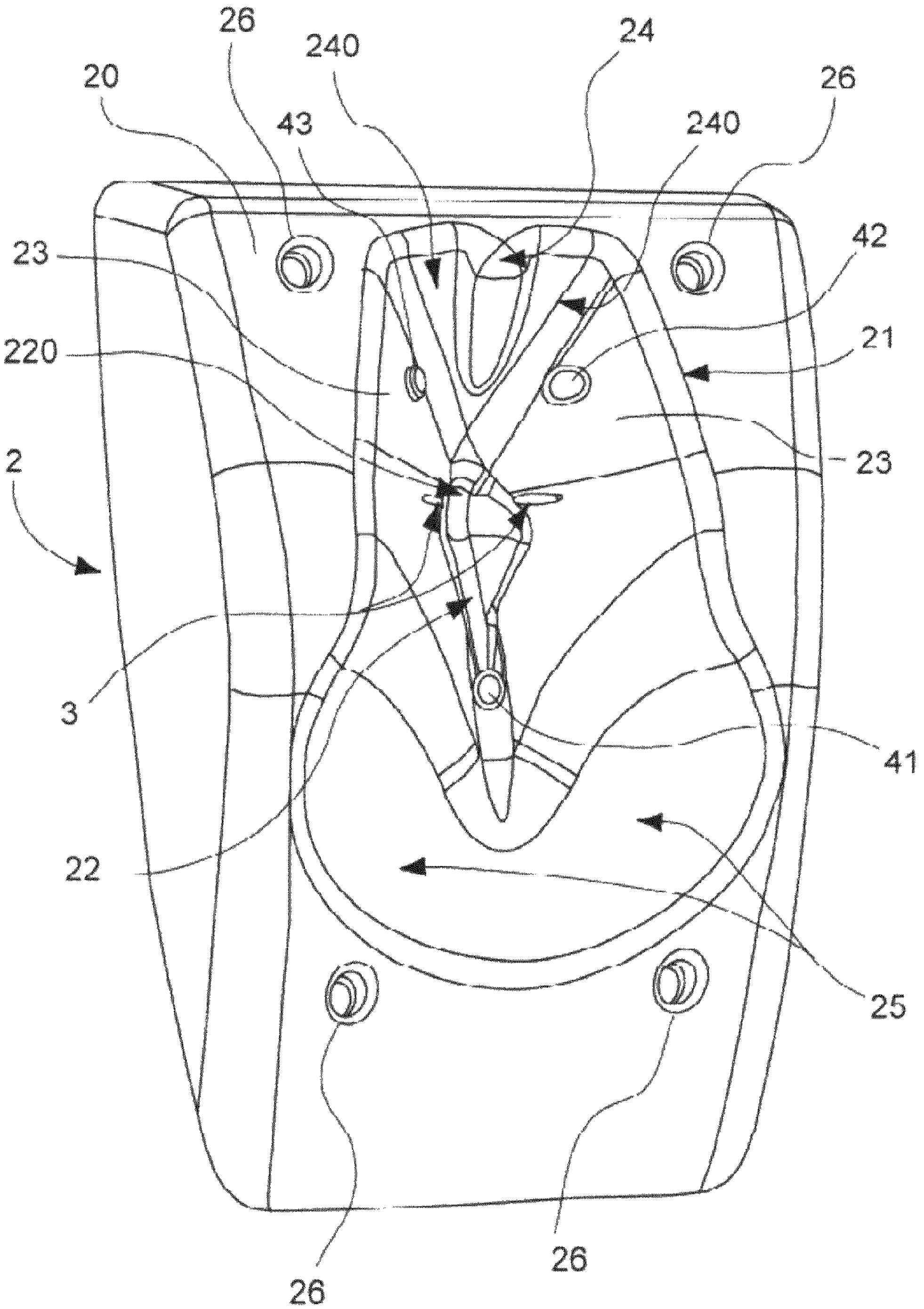

With reference to FIGS. 2 and 3, a retention member 2 of a device according to the invention is described.

According to the present embodiment, the retention member is a part produced by moulding, using a mould particularly produced according to an imprint of the body of the target fowl.

Such a retention member 2 thus has a general surface 20 wherein a cavity is formed, the anatomic shape 21 of which is suitable for conforming to the body of the fowl.

As illustrated, two holes 3 are formed in the retention member, said holes each forming a passage across which a needle can be translated from one position at the rear of the retention member to an injection position (in which the needle protrudes inside the anatomic shape 21 by presenting a needle length of approximately 10 mm therein), or conversely.

It is noted that the presence of two holes enables the use of the device according to the invention to carry out injections of two separate products. However, it is also possible to envisage such a device with a single hole, which is suitable for injecting a single product or for injecting two products via the same injection needle.

According to the principle of the invention, the retention member further comprises:

- means 22 for bracing the detectable bone, in this instance the breast-bone;
- a bearing surface 23, against which the body of the fowl is to be pressed at the muscle(s) to receive the injection;
- sensors 41, 42, 43, the locations of which are explained in more detail hereinafter.

The means 22 for bracing the fowl thus correspond to the deepest area of the anatomic shape 21, and extend over a length corresponding substantially to that of the median part of the breast-bone. Furthermore, the cleft formed by the bracing means 22 comprises one end 220 forming with the adjacent bearing surface 23 a very marked interruption in the slope, such that said end 220 forms an abutment against which the end 11 of the breast-bone 1 is suitable to rest.

Formed in this way, the bracing means 22 form a space for receiving and abutting the breast-bone of the fowl.

Furthermore, the bearing surface 23 extends on either side of the bracing means 22, from same, to the base surface 20, defining a shape corresponding to the breast 10 of the fowl.

Here again, it is noted that, in the case of a device suitable for performing a single injection (the retention member in this case having a single hole 3), it is possible to envisage the retention member comprising a bearing surface 23 extending only on one side of the bracing means 22, said side obviously corresponding to the side of the breast comprising the muscle wherein the injection is to be carried out.

Furthermore, the anatomic shape 21 of the retention member 2 preferentially comprises:

- a complementary bracing protuberance 24, corresponding to the space between the clavicles 12 of the fowl and on either side of which the pectoral muscles of fowl are to be pressed;
- a complementary bearing surface 25, against which the thighs of the fowl are to be pressed, at least partially, said surface 25 defining an extended part of the anatomic shape 21 so as to correspond to the shape of the thighs of the fowl.

According to the present embodiment, the anatomic shape 21 thus extends from the base surface 20 and includes bracing means, the bearing surface 23, said surface extending to the ends of the bracing means 22 such that the protuberance 24 (and the surfaces 240 for receiving the pectoral muscles) and the surface 25 are provided in the anatomic shape 21.

As specified above, the anatomic shape 21 of the retention member 2 is provided with sensors 41, 42, 43.

These sensors are arranged in the retention member such that each hole is provided between two sensors.

Furthermore, the arrangement of the sensors ensures that the fowl is positioned perfectly in the retention member.

For this, it is necessary to detect the presence of the breast-bone in the bracing means 22 and the pressing of the breast of the fowl against the bearing surface 23. In this way, as illustrated by FIGS. 2 and 3, the sensors are arranged as follows:

- one sensor 41 is positioned in the bracing means 22;
- one sensor 42, 43 is positioned on the bearing surface 23, such that each hole 3 is provided between two sensors (the sensors 41 and 42 for one of the holes and the sensors 41 and 43 for the other hole).

Therefore, it is understood that the presence of at least two sensors combined with a retention member having an anatomic shape conforming to the body of the fowl firstly makes it possible to guide the correct positioning of the fowl in the retention members and, secondly, only activate the injection if the body of the fowl is indeed correctly positioned in the retention member.

This correct positioning of the fowl, whether in relation to the target area to be injected or the injection depth, is verified by actuating the two sensors between which the hole across which the injection needle is moved extends.

Indeed, due to the anatomic shape of the retention member, the two sensors on either side of the hole can only be activated simultaneously by a single fowl positioned correctly in the retention member. However, the injection is controlled by the simultaneous actuation of two sensors (or of three sensors in the embodiment described hereinafter).

Therefore, this distinguishes the device according to the invention fundamentally from certain devices according to the prior art using a cradle of a rudimentary shape, suitable for receiving the breast of a fowl and inside which a sensor is positioned, against which the breast of the fowl is to be pressed.

Indeed, in such cradles, the activation of the sensor may be obtained by presenting the fowl in a plurality of positions. In any case, these devices according to the prior art do not guarantee a consistent injection in the precise target area of the body of the fowl.

Furthermore, it is noted that the sensors are actuated directly by the fowl itself, unlike a loading sensor of a movable retention member under the weight of a fowl as in the device described by patent document FR-2 276 839.

In the configuration of the device whereby said device has two holes for inserting injection needles, the sensors 41, 42, 43 are thus arranged in a V shape, the sensor 41 positioned in the bracing means 22 occupying a position corresponding to the base of the V, each hole 3 extending (at least partially) on one arm of the V.

Obviously, the sensors 41, 42 and 43 are presented in the form of an extra thickness in relation to the surface whereon they are positioned, the surface of the bracing means 22 and the bearing surface 23 respectively. However, this extra thickness is minimal such that the sensors are flush with the surface of the retention member so as to be activated only when the corresponding part of the body of the fowl is pressed perfectly against the surface of the retention member.

It is noted that, as seen clearly in FIGS. 2 and 3, the holes 3 have an oblong shape, such that the position of the needle can be adjusted on the length of the corresponding hole.

Figure 4:
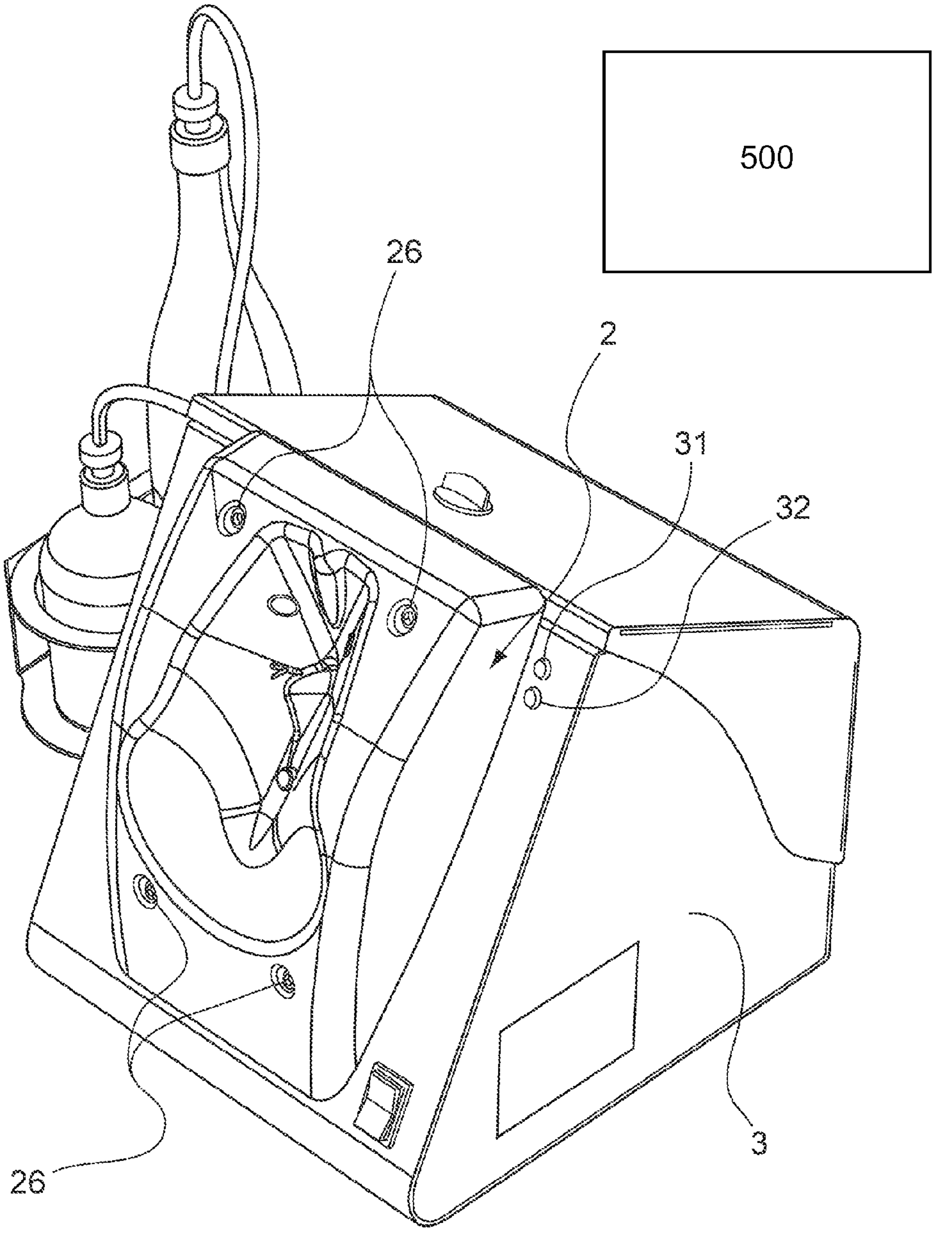
FIG. 4 is a perspective general view of a device according to the invention, on the retention member side.
Figure 5:
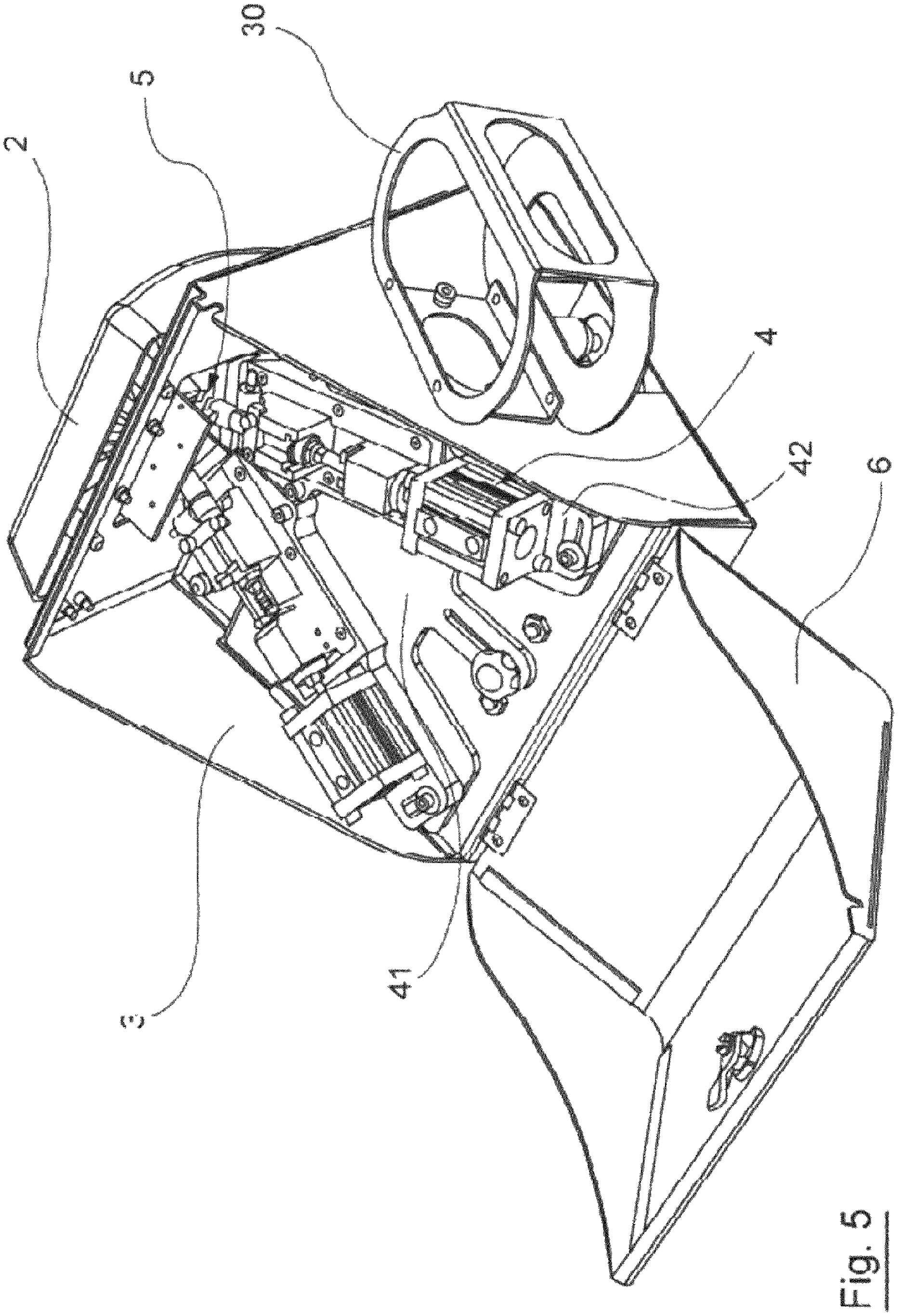
FIG. 5 is a general perspective view of a device according to the invention, on the rear hatch side.

FIGS. 4 and 5 illustrate a device according to the invention as a whole.

As illustrated in these figures, the device comprises a casing 3 particularly including drive means 4 for translating each needle 5.

According to one feature of the device, the retention means 2 are removably mounted on the casing 3, the retention member having for this purpose attachment holes 26 suitable for being traversed by attachment means, such as screws for example.

In this way, according to the morphology of the target fowl (or target bird), it is possible to replace the retention member of the device easily, for example to switch from a retention member such as that illustrated in FIG. 2 which corresponds to the average anatomy of a breeding hen of a predetermined age, to a retention member such as that illustrated in FIG. 3 corresponding to the average anatomy of a laying hen (generally having a smaller build than breeding hens) of a predetermined age (a vaccination campaign is generally conducted when the hens are between 10 and 20 weeks of age).

Furthermore, it is also possible to disassemble the retention member quickly and easily with a view to cleaning same.

Moreover, the casing has a rear hatch 6 giving access to the components fitted inside the casing, and in particular the drive means 4. As illustrated, the casing 3 comprises support means 30 suitable for receiving containers containing the veterinary products to be dispensed.

The drive means 4 are mounted on a plate 41 attached removably in the casing 3, the plate 41 needing to be moved (back) to be able to access the syringes.

Furthermore, the drive means 4 are attached on the plate 41 by means of a supporting member 42 the position of which may be adjusted on the plate 41 so as to modify the position of the needle in relation to the oblong holes.

To perform the injection, the operator takes hold of an animal by the wings and legs, so that the fowl can be presented on the device by inserting the breast thereof into the retention member, keeping said fowl extended. After correct positioning in the mould, the operator presses the fowl against the retention member so as to press the breast-bone against the end 220 of the bracing means 22 and actuate the sensors, which activates the movement of the syringes, followed by the injection of the veterinary product(s).

The device includes an indicator light 31 envisaged to light up when the fowl is positioned correctly in the retention member (i.e. when the sensors are actuated). At the end of the injection, a second indicator light 32 is envisaged to light up.

The movement of the needles may be driven by pneumatic cylinders. The movement of the cylinders and the needles may be controlled by any system with automatic, electronic, programmable operation, or any other operation well-known to those skilled in the art, to provide a predefined injection range and adjust the penetration distance of the needles in the muscles according to the size of the muscles to be injected and the target birds. The needles may be connected to a pump or hydraulic precision syringe that can deliver a precise volume in each needle and is capable of repriming and expelling any bubbles. This device is controlled by an automatic controller powered by batteries. The automatic controller handles the injection cycles. In this way, each injection is counted, and after each injection, the syringes are filled automatically with a product dose. The automatic controller is configurable such that the device is used to perform two injections (one on each side of the detectable bone such as the breast-bone for example) or a single injection. Each needle may have a disinfection system which can be used after one or more intramuscular injections. A disinfection fluid may for example be released onto the contaminated needle and subsequently be disposed of before the next injection.

The kit may advantageously further comprise a set of syringes, vials, bags or suitable packaging for veterinary products and/or vaccines 500. The avian injection or vaccination kit may also comprise a technical data sheet and instructions on the vaccination and/or treatment methods and on the use of said device 500.

The invention claimed is:

1. A device for injecting veterinary products to at least one fowl by intramuscular injection, wherein said injection(s) can be carried out in the area of at least one muscle in the vicinity of a bone having a detectable shape in the body of said fowl, said device comprising:

a retention member with means for bracing said detectable bone, at least one hole formed in said retention member, at least one injection needle, said needle(s) being movable across said hole, characterised in that said retention member has:

an anatomic shape comprising a cavity that conforms to said body of said fowl and inside which said bracing means are provided, said anatomic shape comprising a bearing surface for said body at said muscle, at least two contact sensors to be actuated by said fowl and provided on said anatomic shape with at least one on said bearing surface, said hole(s) being provided between said sensors, said sensors being activated only if said fowl is positioned in the device so that an anatomic area of said fowl that corresponds to said anatomic shape is correctly positioned in said anatomic shape.

2. The device according to claim 1, characterised in that said retention member has two holes each forming a passage across which an injection needle is movable, said bracing means extending between said holes.

3. The device according to claim 1, characterised in that one of said sensors is positioned in said bracing means.

4. The device according to claim 1, characterised in that said anatomic shape consists of the breast of said fowl, said bracing means forming a space for receiving and abutting the breast-bone of the fowl.

5. The device according to claim 4, characterised in that said anatomic shape extends from said space for receiving and abutting a fowl breast to a complementary bracing protuberance against which a cavity between clavicles of said fowl is to be pressed.

6. The device according to claim 4, characterised in that said anatomic shape extends from said space for receiving and abutting a fowl breast to a complementary bearing surface corresponding to the shape of at least one thigh of said fowl.

7. The device according to claim 1, characterised in that it comprises three contact sensors to be actuated by said fowl, said three sensors being arranged in a V shape, the base of said V shape being occupied by said sensor positioned in said bracing means.

8. The device according to claim 7, characterised in that each of said holes extends at least partially on one arm of said V.

9. The device according to claim 1, characterised in that said retention member is removably mounted on a casing including means for driving said needle(s).

10. The device according to claim 9, characterised in that said casing has a rear hatch for accessing said drive means.

11. The device according to claim 1 for the vaccination, treatment and/or prevention of avian diseases, and/or for welfare.

12. The device according to claim 11, characterised in that the avian diseases are avian influenza, SARS, avian malaria, Newcastle disease, mycoplasmosis, cholera, Gumboro disease, chicken pox, candidiasis, aspergillosis, salmonellosis, enteritis, bronchitis, pancreatitis, Marek disease, diseases caused by reovirus and/or astrovirus infections, leucosis, or infectious anaemia.

13. The device according to claim 11 for preventing and/or treating infections and contaminations in poultry farms.

14. A Poultry injection and/or vaccination method comprising the steps consisting of (i) taking hold of said poultry, positioning same on the device according to claim 1, such that the part of the body of the fowl completely conforms to the anatomic shape of the retention member, and (iii) pressing said fowl positioned in this way against said retention member such that a reference bone close to the muscle to be injected is pressing against the end of the bracing means thus actuating the sensors, the movement of the syringes and the injection of the veterinary product(s).

15. An avian injection and/or vaccination kit comprising a device according to any of claims 1 to 10 and a series of removable retention members having varied anatomic shapes suitable for the different parts of the body and detectable bones of said fowl.

16. An avian injection and/or vaccination kit according to claim 15, characterised in that it comprises a set of syringes, vials, bags or suitable packaging for veterinary products and/or vaccines, and/or a technical data sheet and instructions.

* * * * *